United States Patent
Farber

(10) Patent No.: US 10,436,739 B1
(45) Date of Patent: Oct. 8, 2019

(54) LOW COST, FAST AND SENSITIVE NOX AND NH3 SENSOR

(71) Applicant: Boris Farber, Solon, OH (US)

(72) Inventor: Boris Farber, Solon, OH (US)

(73) Assignee: BJR Sensors LLC, Solon, OH (US)

( * ) Notice: Subject to any disclaimer, the term of this patent is extended or adjusted under 35 U.S.C. 154(b) by 628 days.

(21) Appl. No.: 14/875,772

(22) Filed: Oct. 6, 2015

Related U.S. Application Data

(60) Provisional application No. 62/060,034, filed on Oct. 6, 2014.

(51) Int. Cl.
  *G01N 27/407* (2006.01)
  *G01N 27/406* (2006.01)
  *G01N 27/41* (2006.01)
  *G01N 33/00* (2006.01)

(52) U.S. Cl.
  CPC ..... *G01N 27/4065* (2013.01); *G01N 27/4062* (2013.01); *G01N 27/4067* (2013.01); *G01N 27/4071* (2013.01); *G01N 27/4074* (2013.01); *G01N 27/4075* (2013.01); *G01N 27/41* (2013.01); *G01N 33/0037* (2013.01); *G01N 33/0054* (2013.01)

(58) Field of Classification Search
  CPC .......... G01N 27/4065; G01N 33/0037; G01N 33/0054
  See application file for complete search history.

(56) References Cited

U.S. PATENT DOCUMENTS

2005/0284772 A1* 12/2005 Farber ............... G01N 27/4065
  205/775

OTHER PUBLICATIONS

Kobayashi et al., "Development of Simultaneous NOx/NH3 Sensor in Exhaust Gas," Mitsubishi Heavy Industries, Ltd. Technical Review vol. 38 No. 3 (Oct. 2001), pp. 126-130.*

* cited by examiner

*Primary Examiner* — Alexander S Noguerola
(74) *Attorney, Agent, or Firm* — John D Gugliotta

(57) ABSTRACT

A unique solution to measure NOx emissions is achieved less expensively and with much greater sensitivity than commercially available NOx sensors. A sensor's active materials are modified and operational algorithms are used to concurrently measure single ppm levels of NOx and NH3 with response times of one second or less. A combined NOx/NH3 sensor to have much finer control of an SCR system, thereby reducing NOx emissions and ammonia slip in a closed-loop device, all at lower cost than the current state-of-the-art solutions.

3 Claims, 14 Drawing Sheets

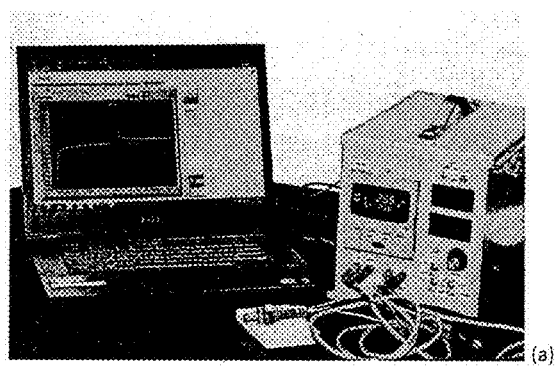
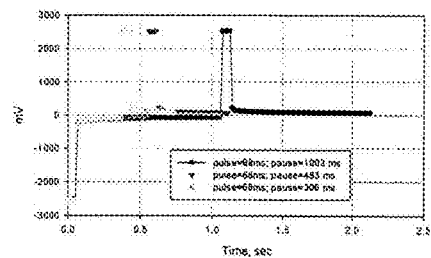
Figure 10(a)
Figure 10(b)
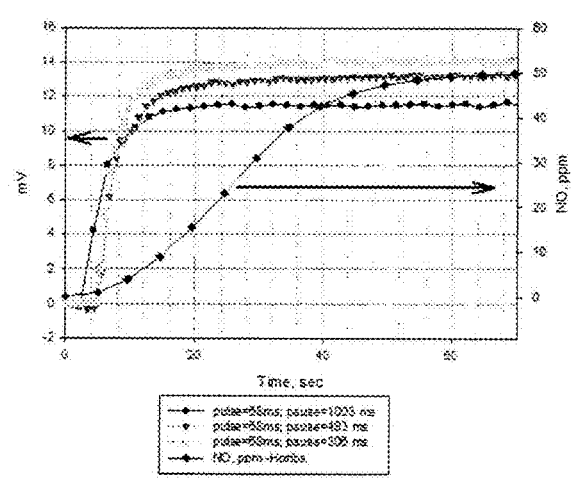
Figure 10(c)

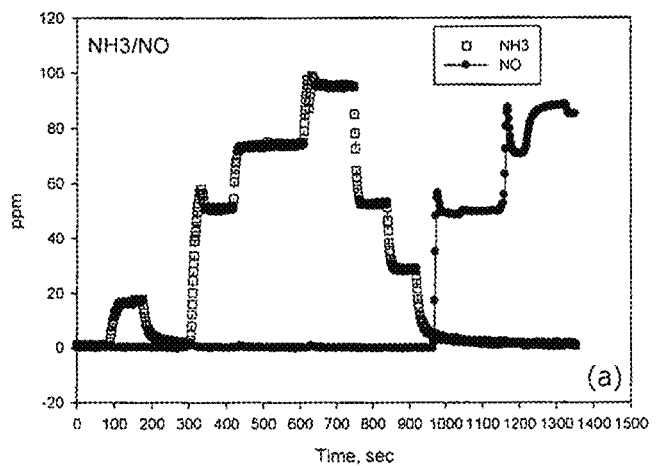
Figure 19(a)
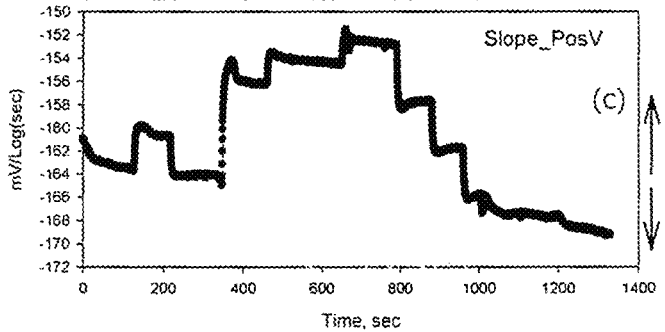
Figure 19(b)
Figure 19(c)

LOW COST, FAST AND SENSITIVE NOX AND NH3 SENSOR

RELATED APPLICATIONS

The present invention claims benefit of U.S. Provisional Application No. 62/060,034 filed on Oct. 6, 2014 and incorporated by reference as if fully rewritten herein.

BACKGROUND OF THE INVENTION

1. Field of the Invention

The present invention relates generally to the measurement of NOx emissions and, more particularly, to a zirconia sensor capable of detection of NOx and NH3 with high sensitivity and fast response.

2. Description of the Related Art

In order to meet EPA's 2010 NOx emission standards, most diesel engine manufacturers utilize Selective Catalytic Reduction, or "SCR" exhaust after-treatment systems. The SCR enables an engine to operate under optimized combustion conditions (high temperatures, high peak pressure, and excess oxygen), which improves fuel efficiency but produces elevated levels of NOx. The SCR system reduces NOx concentrations in the exhaust stream by >95% through a catalytic reaction with NH3 that produces nitrogen and water. A NOx sensor is installed downstream of the SCR catalyst to provide closed loop feedback to the urea doser.

The efficacy of the SCR system depends on the sensitivity, accuracy and response time of the NOx sensor. In the present state-of-the-art, a typical NOx sensor of the type produced by NGK Spark Plug Co., Ltd. of Nagoya, Japan (NGK) can only measure NOx levels of >10 ppm with a specified accuracy of +/−10 ppm. In addition, the NGK sensor uses a stacked ceramic layer design, which is complicated, expensive and subject to thermal and mechanical shock.

Furthermore, the NGK sensor cannot distinguish between NOx and NH3, which makes it difficult for the SCR system to detect ammonia slip. A separate NH3 sensor can be used to control ammonia slip, but it further increases cost and complexity of the SCR system.

Although the current NGK NOx sensor has sufficient sensitivity to meet current EPA NOx standards, California's Air Resources Board (CARB) recently released its "Vision for Clean Air" which calls for reducing NOx emissions from heavy duty vehicles by at least 80% by 2023. Because California has the authority to promulgate its own NOx regulations, SCR systems and NOx sensors will have to be significantly improved if CARB's aggressive vision is implemented.

The current NGK NOx sensor is not sufficient to meet CARB's goals. In addition, the NGK NOx sensor has reached its design limits and thus it will be necessary to find a new, cost effective and durable technology that delivers accurately detect single ppm levels of NOx.

It is thus an object of the present invention to provide a sensor and method of making the same that has a similar sensitivity to both NOx as well as NH3 within a vehicle's engine exhaust.

It is another object of the present invention to provide a zirconia sensor capable of detection of NOx and NH3 with high sensitivity and fast response than commercially available sensors.

It is a further object of the present invention to provide such a sensor that concurrently measure single ppm levels of NOx and NH3 with response times of one second or less.

It is yet another object of the present invention to optimize a sensor electrode structure by adjusting parameters of a pulse discharge technique via a filtering algorithm in order to differentiate response to NOx and NH3.

It is still further objects of the present invention to enable a combined NOx/NH3 sensor having much finer control of an SCR system and thereby reducing NOx emissions and ammonia slip in a closed-loop device, all at lower cost than the current state-of-the-art solutions.

Some methods and devices are known that incorporate a pulse discharge technique in the development of gas sensors. For example:

U.S. Pat. No. 7,585,402 issued to the present inventor, describes an improved oxygen sensor and a method of sensor conditioning for improving signal output stability and differentiation between responses to different gases such as exhaust from combustion processes. A square wave (or saw tooth) voltage pulses of opposite polarity and equivalent amplitude are applied between sensor electrodes. Pulses are separated by pauses, when charging power supply is disconnected from the sensor and sensor discharge is recorded. Useful information regarding concentration of analyzed gases can be extracted from measuring open circuit voltage decay during the pause immediately following voltage pulse, as well as measuring the charging current during positive (negative) pulses and the discharging current during pauses following voltage pulses.

U.S. Pat. No. 8,110,080, also issued to the present inventor, describes a method for activating a zirconia oxygen sensor which detects the oxygen concentration of an ambient atmosphere by means of a zirconia element that has a porous electrode formed on both sides of an impervious oxygen ion conductor.

An electrical current is applied as a pulsed, square wave, direct current during heat up, heat soak, and cool down of the ionic conductor that is applied to ceramic substrate, thereby causing oxygen ions to flowing through the sensor body and pumping oxygen gas through the sensor electrodes, thus improving electrode porosity distribution.

Consequently, a need has been felt for providing an apparatus and method for the measurement of NOx emissions using a zirconia sensor capable of detection of NOx and NH3 with high sensitivity and fast response.

SUMMARY OF THE INVENTION

A Pulse Discharge Technique (PDT) has been utilized to develop a suitable low cost robust zirconia lambda sensor to measure single ppm NOx concentrations with response times of less than 1 second. The system is capable of detection of NOx and NH3 with high sensitivity (<1 ppm) and fast response ~1 sec. The system further demonstrates similar sensitivity to both exhaust components. By adjusting parameters of the PDT and optimizing electrode structure and composition, a filtering algorithm is used to differentiate response to NOx and NH3. The sensor can accurately detect NOx levels in combustion exhaust from 0.5-1000 ppm with response times of less than 1 second (which is the required to insure proper dosing of the SCR catalysts in response to changes in NOx levels). Concurrently measuring ppm levels of NH3, this dual capability permits a much finer control over the SCR systems and thereby reduce NOx levels and detect ammonia slip conditions.

Further features of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 10a shows a typical hardware package for conducting the PDT of the present invention;

FIG. 10b depicts charge/discharge cycles;

FIG. 10c depicts the corresponding speed of response curves;

FIG. 19a depicts time dependence of NO and NH3 concentration under the following test conditions: O2=10%; H2O=8%; CO2=8%; Pulse=51 ms; Pause=119 ms, Pulse amplitude=2.5V;

FIG. 19b depicts slope of the discharge curves following negative voltage pulse applied to the inner (reference electrode) of the lambda sensor;

FIG. 19c depicts slope of the discharge curves following positive voltage pulse applied to the inner (reference electrode) of the lambda sensor;

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
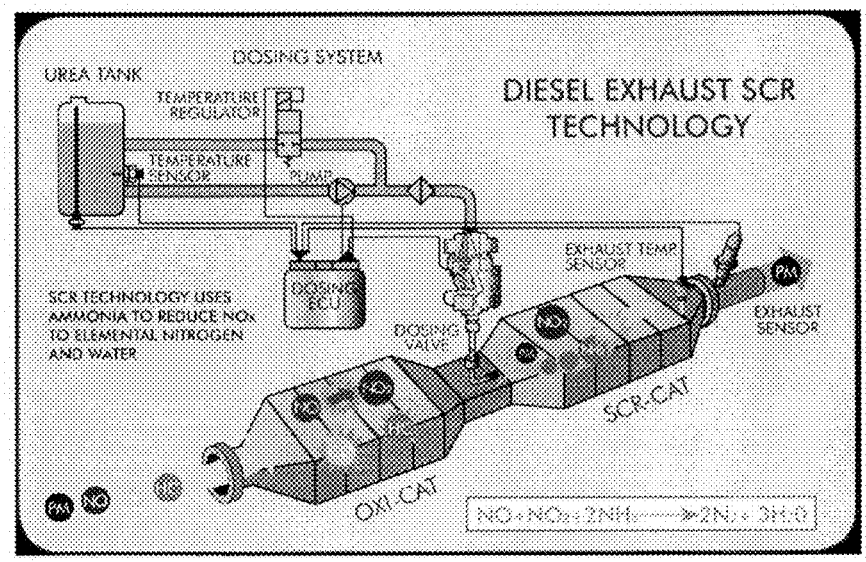
FIG. 1 is an SCR catalytic converter according to the PRIOR ART.

To meet the EPA 2010 NOx emission standards in diesel engines, a number of diesel engine manufacturers have relied on selective catalytic reduction (SCR) exhaust after-treatment systems. The selective catalytic reduction (SCR) method enables engines to operate under optimized combustion conditions (high temperatures, high peak pressure, and excess oxygen), which resulted in improved fuel efficiency. In the SCR systems, a urea-water solution (AdBlue™) is injected into a SCR Catalyst. On the surface of a catalyst it decomposes into NH3 and CO2. NOx reacts with NH3 to produce nitrogen and water as illustrated in FIG. 1. Efficiency of NOx removal depends on multiple factors: temperature, oxygen content, gas velocity, residual concentration of NH3 stored on the catalyst and catalytic activity of the SCR materials.

Since in automotive applications transient conditions are the norm, close loop control is required to maintain specified NOx conversion efficiency through dosing the catalyst with the appropriate amount of urea. For optimum functionality of the SCR system, both residual NOx and NH3 concentrations needs to be measured downstream from the SCR catalyst to maintain minimum NOx concentration and avoid ammonia slip from overdosing the catalyst.

Current EPA regulations and the California Air Resources Board's Vision for Clean air initiative put stringent requirements on the performance of the after-treatment system and hence requires detection of low concentrations of NOx and NH3 sensors to optimize SCR systems. Achievable low detection limits for the sensors are: 1 ppm (of NOx/or NH3) with the speed of response of ~1 s. Multiple attempts have been made over the years to develop sensors for the separate detection of NOx and NH3. Most of these attempts have resulted in proposed sensors utilizing a zirconia based electrolyte with different electrodes having varying catalytic activity measuring essentially derivatives of oxygen concentration that change as a result of concurrent reactions with NOx or NH3. Both amperometric and potentiometric type of sensors have been suggested, with the most promising so far appearing to be sensors based on a planar multilayer ceramic platform with multiple cavities and catalytic electrodes.

Figure 2:
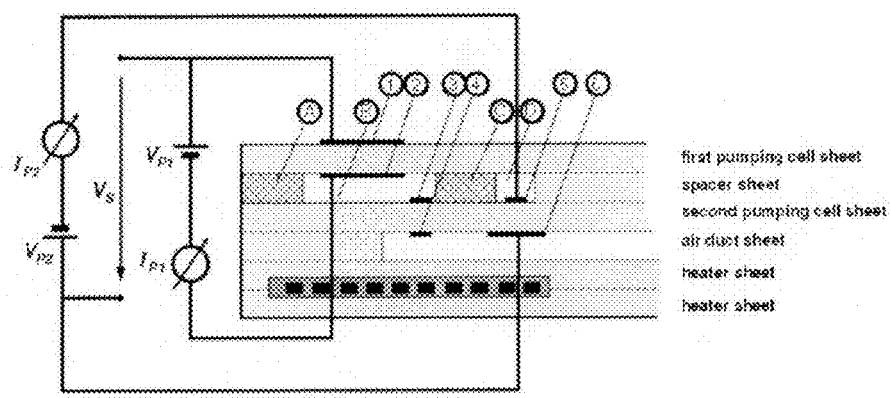
FIG. 2 is an NGK-NOx sensor schematics according to the PRIOR ART.

An amperometric NOx sensor was commercialized by NGK. Such a sensor structure is shown in FIG. 2. Consisting of 6 layers of ceramic and two diffusion barriers separating two chambers, in the first chamber all the excess oxygen is pumped out from the exhaust sample. The remaining NOx diffuses through the second barrier into the next chamber, where it get electrochemically decomposed on the surface of cathode due to applied pumping voltage. Resulting current is directly related to the amount of oxygen formed during the decomposition of NOx per reaction (1):

$$2NO + 4e^- \rightarrow N_2 + 2O^{2-} \qquad (1)$$

A significant problem of these sensors is related to a very small electronic current that occurs as a result of NOx decomposition. A rough estimation predicts the NOx sensitivity in the range of ~nA/ppm of NOx. Due to this extremely low current signal level, it strongly interferes with a leak current from the sensor heater. Typical resolution of this sensor is >10 ppm with the specified accuracy of +/−10 ppm and a response time of 1.3-1.7 sec.

As shown in FIG. 2 the sensor structure is very complex and is correspondingly rather expensive. Additional complications are related to a potential thermal shock due to direct contact with liquid water. As a result, exhaust system has to be pre-heated to above the dew point temperature causing a lag in the availability of NOx measurements.

Figure 3:
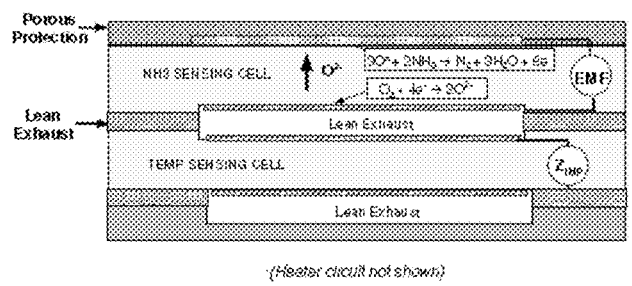
FIG. 3 is a schematics of a Delphi® NH3 sensor according to the PRIOR ART.

Ammonia sensor for close loop SCR control was developed by Delphi during the last decade. The sensor schematic is shown in FIG. 3. Similar to NGK sensor it is based on a planar type design and has to be protected from direct contact with liquid water due to thermal shock. System algorithm is disabling the sensor heater at temperatures below the dew point. Functional temperature range of the sensor is from 200-450° C., specified measurement range: 0-100 ppm of NH3 with a tolerance +/−5 ppm above 10 ppm level. Speed of response is 5 s.

Sensor operation is based on a mixed potential response of the sensor electrodes (see FIG. 3). Sensing electrode is made from SCR active materials (vanadium oxide, molybdenum oxide, tungsten oxide etc.). The following reactions are taking place at the sensing and reference electrodes:

$$\frac{1}{2}O_2 + 2e^- \rightarrow O^{2-} \qquad (2)$$

$$O^{2-} + \frac{2}{3}NH_3 \rightarrow H_2O + \frac{1}{3}N_2 + 2e^- \qquad (3)$$

where O2− is the oxide ion. The potential difference between the two electrodes produces an EMF output, which is logarithmically proportional to NH3 concentration.

As was reviewed above, both of these types of sensors are not quite meeting the desired accuracy (~1 ppm) and the speed of response (~1 s) for NOx or NH3 measurement for optimization of SCR control. Additionally, mechanical robustness of the planar type sensors needs to be improved with a corresponding reduction of the sensor costs.

A zirconia-based potentiometric oxygen sensor (I-sensor), one of the most successfully commercialized sensors of the last century, has greatly improved energy efficiency and reduced pollution from vehicles by measuring oxygen concentration in the exhaust gas. Low cost and reliable I-sensors for NOx measurements also have an attractive commercialization pathway because they are based on a widely deployed commercial technology.

Figure 4:
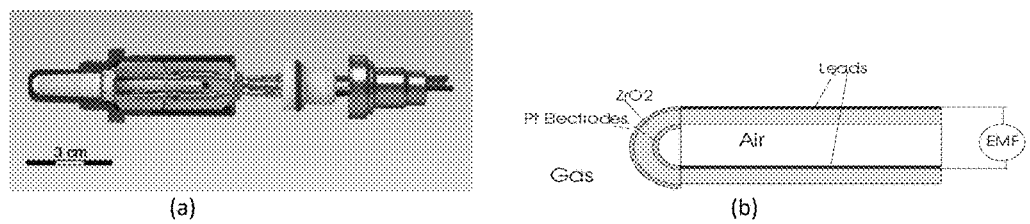
FIG. 4 is a schematic of a thimble type zirconia lambda sensor according to the PRIOR ART.

A typical design of the I-sensor is shown in FIG. 4 and includes an impervious zirconia ceramic substrate separating two Pt electrodes exposed to analyzed gas and internal ambient air reference. Inside a thimble substrate a pencil heater is positioned to speed up sensor heat up time and maintained pre-defined sensor operating temperature. Stabilized zirconia heated to above 350° C. is demonstrating sufficient ionic conductivity for oxygen concentration measurements in the combustion exhaust. Oxidation/reduction reaction of oxygen on the surface of Platinum electrodes give rise to voltage output in case of different oxygen partial pressures on the process and reference sides of the sensor. At high enough temperatures T>550° C., diffusivity of oxygen on the surface of Pt electrodes is high and the voltage output of the I-sensor is related only to the changes in oxygen concentration. At lower temperatures T<500° C., oxygen diffusivity is low enough and other gases (NO, NOx, NH3, H2, CO etc.) can take part in the electrochemical oxidation/reduction reactions on the surface of Pt electrodes, and the output of the λ-sensor becomes dependent on the minor constituents of the exhaust. This regime of oxygen sensor operation is called "mixed potential". So far attempts to utilize λ-type mixed potential sensors for NOx measurements were not successful due to signal drift and repeatability problems. Additional complications in utilizing mixed potential sensors with Pt electrodes for detection of minor components in the exhaust is related to high catalytic activity of platinum, which is not specific enough to any particular minor exhaust component, resulting in high cross-sensitivity to different gases (NOx, CO, H2 etc).

Figure 5:
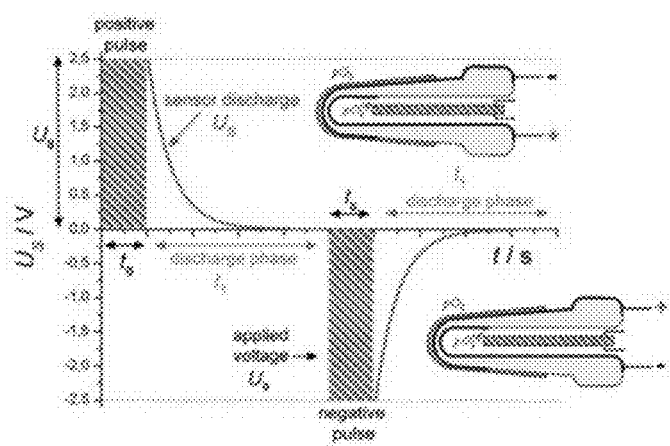
FIG. 5 is a schematic of the Pulse Discharge Technique according to the preferred embodiment of the present invention.
Figure 6:
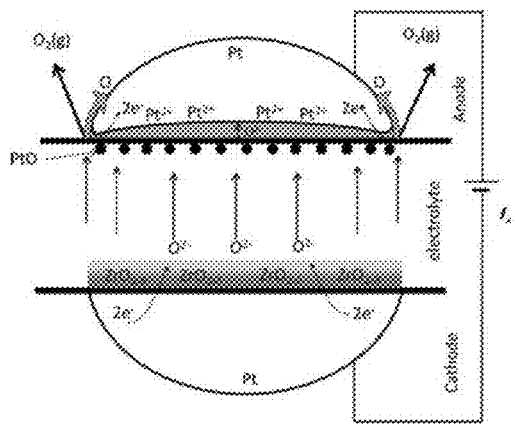
FIG. 6 is an electrochemical processes during polarization of Pt electrodes.

To improve signal stability and reduce cross-interference between different exhaust components in the output of a mixed potential sensor, a Pulse Discharge Technique (PDT) is employed. PDT involves charging a sensor by a sequence of voltage pulses of opposite polarity and equal amplitude applied between the sensor electrodes (see FIG. 5). After each pulse sensor electrodes are disconnected from the charging source and open circuit discharge curves are measured following the pulses. This approach provides solution for several problems related to measurements with mixed potential sensors. During polarization of electrodes during the voltage pulse (see FIG. 6) oxygen ions are pumped from the cathode to the anode of the lambda sensor. At the cathode, zirconia electrolyte is partially reduced, while at the anode-platinum oxide is formed. These two processes deliver fresh oxygen ions to the reaction sites and partially reduce zirconia in the opposite cycle, correspondingly cleaning reaction interfaces for redox reactions (see equations 1-3) and improving signal output stability. Formation and reduction of platinum oxide during polarization cycles make sensors uniquely suitable for detection of NOx and NH3.

Figure 7:
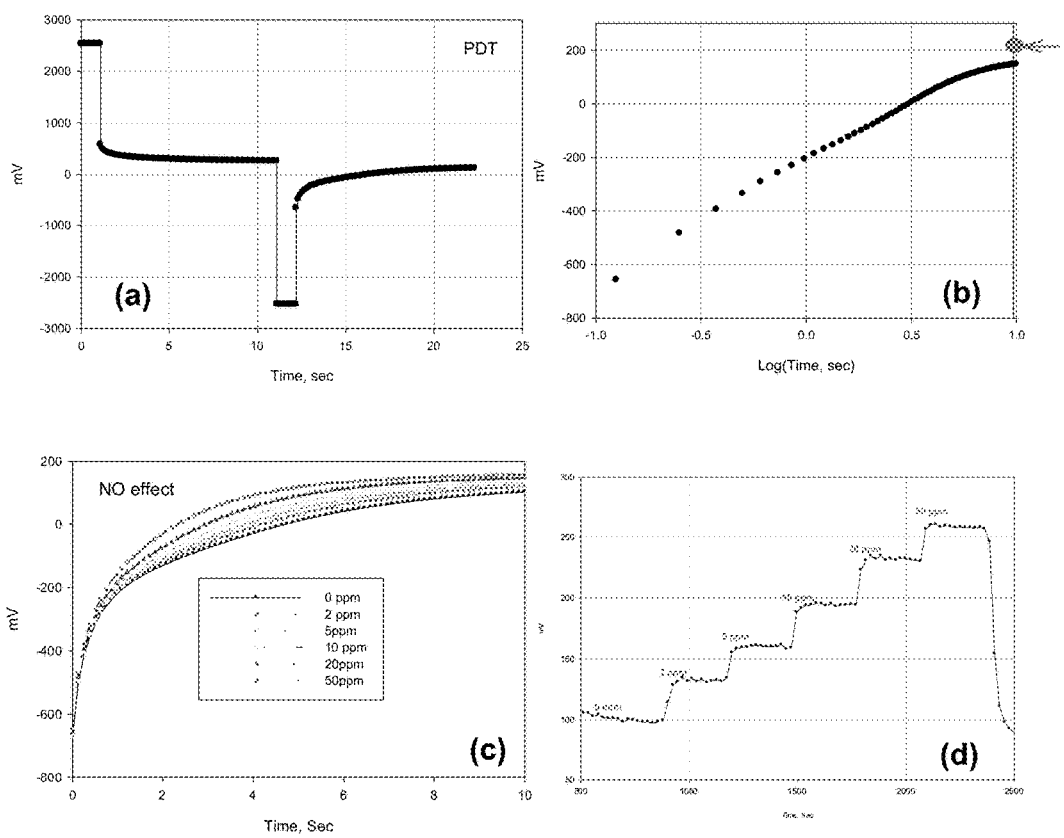
FIG. 7 depicts NO measurement with PDT.

FIG. 7 show an example of NO measurements with PDT. Applied pulses are shown in FIG. 7a. Zirconia based I-sensor can be represented by an electrochemical capacitor and the discharge curve can be approximated by a straight line in Voltage Log(t) coordinates (where t is the time during the pause). From the regression line, a slope and a constant of the fitted curve can be determined. Sensor output in the pulse discharge technique is defined as the voltage extrapolated to the defined pause duration of 10 sec (see FIG. 7(b)). It is observed that the kinetic of the sensor discharge is strongly affected by the presence of very small concentration of NO. FIG. 7(c) shows faster discharge curves with increasing concentration of NO starting from 2 ppm. FIG. 7(d) shows extrapolated mV sensor output.

Figure 8:
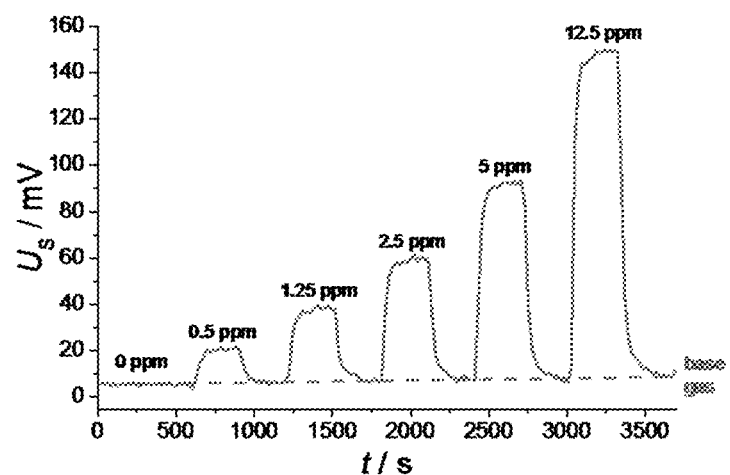
FIG. 8 shows sensor response at different NO contents in the concentration range of 0.5 to 12.5 ppm.
Figure 9:
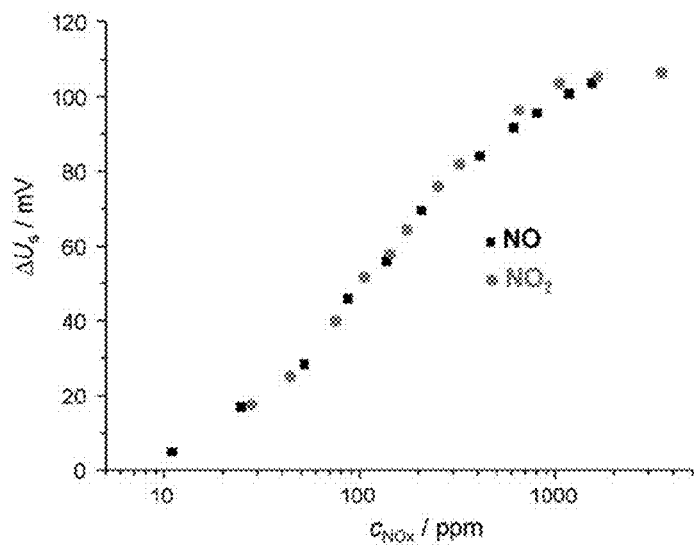
FIG. 9 shows NO and NO2 Sensitivity (Total NOx)

Sensitivity of PDT is very high, as shown in FIG. 8. Concentration as low as 0.5 ppm of NO can be reliably detected. FIG. 9 demonstrates that PDT is measuring total NOx concentration (Equal response to NO and NO2).

During initial development it was found that the charge/discharge cycles were relatively long (Pulse duration=1 sec/Pause duration=10 sec). This limited speed of response to ~20 sec. New and upgraded hardware/software for PDT is shown in FIG. 10(a). Charge/discharge cycles were reduced down to <1 sec (see FIG. 10(b)), with a corresponding decrease in the speed of the system response to ~1 sec (see FIG. 10(c)).

While it is understood that the mechanism of operation does not need to be definitively understood and disclosed for purposes of enabling the present invention, for purposes of assisting a person having ordinary skill in the relevant art to understand and practice the present invention a proposed mechanism of operation, as understood at the time of the invention, is provided. The most plausible mechanism of PDT sensitivity to NOx is related to platinum oxide formation and its decomposition as a result of reaction with NO and NO2 (see equations 4-7). Platinum oxide formed during the oxidation reaction is unstable and electronically charged. A charge generated during the pulse stage of PDT is stored by formation of PtO—.

Figure 11:
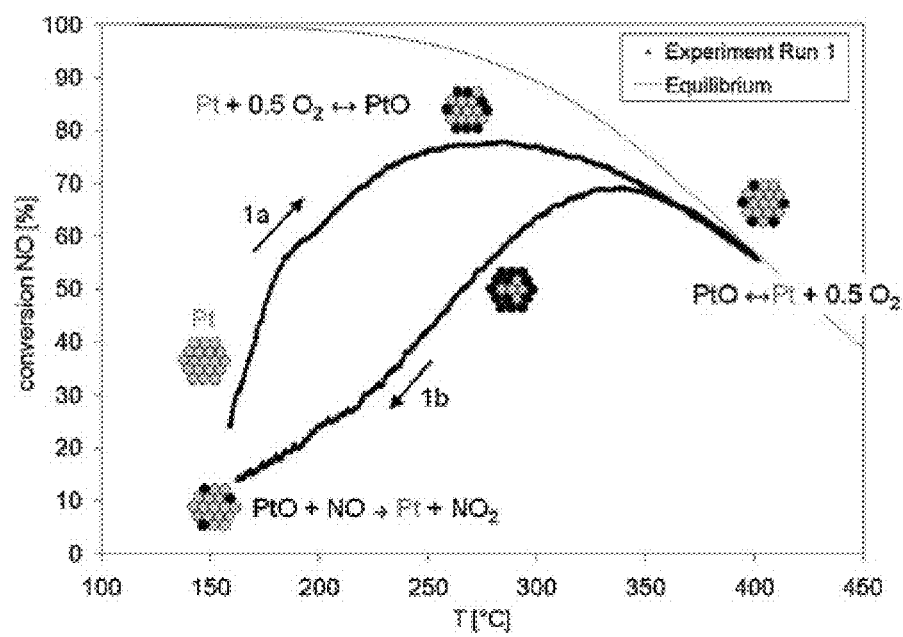
FIG. 11 depicts a mechanism of platinum oxide redox reactions with Nox.

FIG. 11 shows electrochemical reactions taking place during interaction between Pt and NOx. Starting with a clean Pt electrode after a cationic cycle of PDT, platinum oxide is formed by reaction with oxygen ions

$$Pt + xO^{2-} \rightarrow PtO_x + 2xe^-  \quad (4).$$

At high enough temperatures (>450° C.) PtOx is thermally decompose

$$PtO_x + 2xe^- \rightarrow Pt + xO^{2-}  \quad (5).$$

PtO can be also decompose as result redox reactions with Nox:

$$PtO + NO \rightarrow Pt + NO_2  \quad (6)$$

$$PtO + NO_2 \rightarrow PtO_2 + NO  \quad (7).$$

Figure 12:
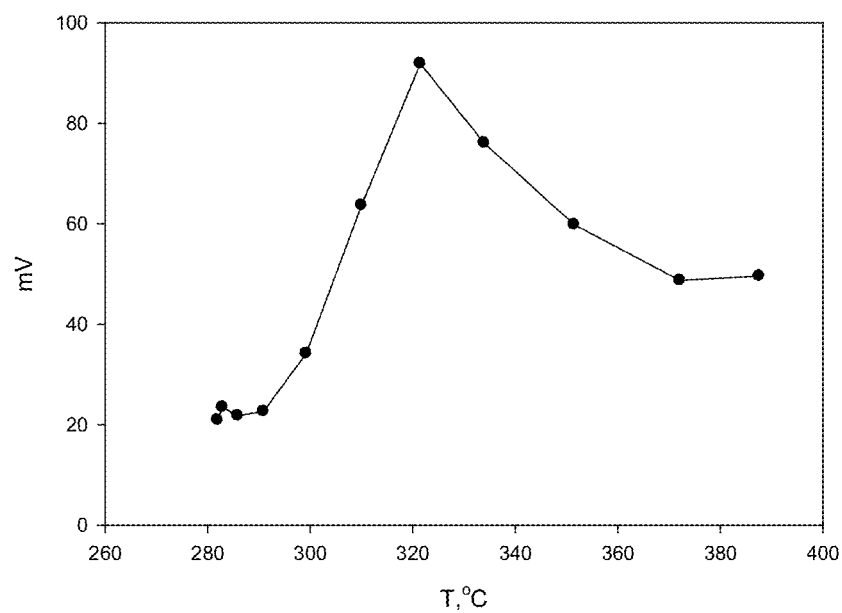
FIG. 12 depicts temperature dependence of the PDT signal at 5 ppm NO.

Since pure Pt and PtO2 are neutral, both of these reactions ((6) and (7)) would lead to charge dissipation observable by PDT. Maximum reaction rates of the type 6-7 are predicted to occur in the temperature range 300-350° C. Convincing confirmation of the above discussed mechanism can be seen in FIG. 12, were is observed a peak in NO sensitivity in the predicted temperature range.

Hauff et al. (See Hauff, Dubbe et al. 2013) have shown that platinum oxide formation and reduction depends only on the temperature and of NO/NO2-ratio under oxygen excess.

Figure 13:
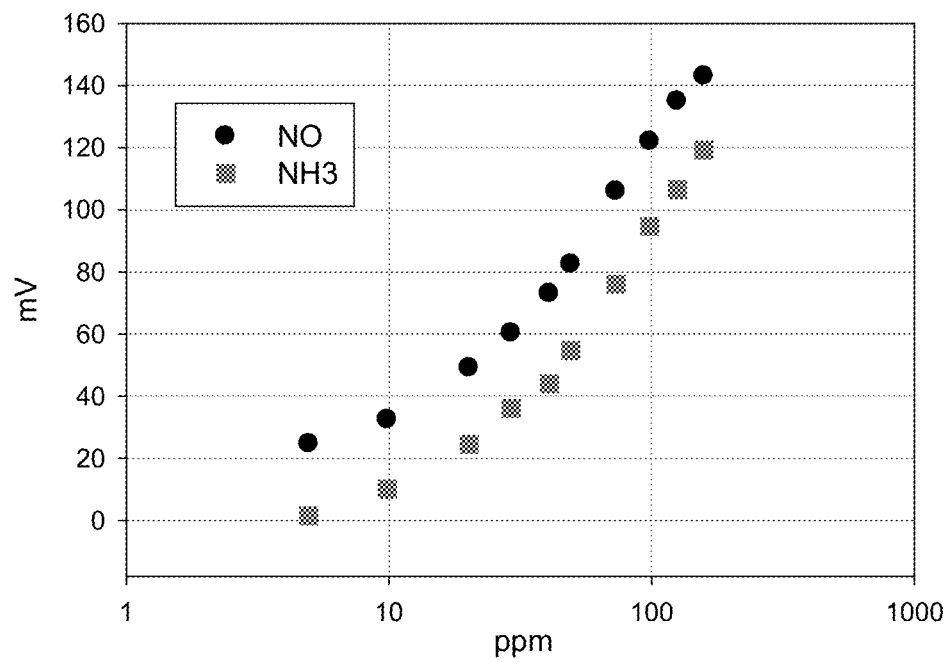
FIG. 13 depicts PDT sensitivity to NO and NH3 applied individually.

High sensitivity of the PDT technique is related to advantages of potentiometric versus amperometric measurements. To detect a single molecule of NO with NGK method, current measurement produced by two electrons is required (see equation 1). On the other hand, voltage change produced by reactions 6 or 7 can be estimated as $$\Delta V \sim \frac{e^-}{C} \quad (8)$$

where C is a capacitance of the I-sensor. Since capacitance of the sensors is ~10-4 F, corresponding amplification ×104 can be achieved for detection of a single NO molecule, which explains high output signal from the I-sensor operated under PDT. Summarizing the advantages of the PDT for NOx measurements:

Based on a thimble type I-sensor with Pt electrodes;
Robust and proven mechanical design;
Well established cost structure ~50% of the planar NOx sensor cost
Properly optimized Pt electrodes has proven long-term durability *Higher sensitivity to NOx<1 ppm;
High selectivity to NOx 2. Operation of the Preferred Embodiment Application of PDT to NH3 sensing is shown in conjunction with FIG. 13-21. FIG. 13 shows cross-sensitivity of I-sensor with Pt electrodes to NH3 under PDT conditions. PDT sensitivity for NH3 measurement is strong (similar to NO). Table 1 shows summary of the results.

TABLE 1

Summary of cross-sensitivity components for different gas

| Gas | Sensitivity Negative Pulse mV/dec | Sensitivity Positive Pulse mV/dec |
|---|---|---|
| NO | 117.5 | 10.5 |
| NO₂ | =NO | |
| NH₃ | 112.5 | 13.5 |

Figure 14:
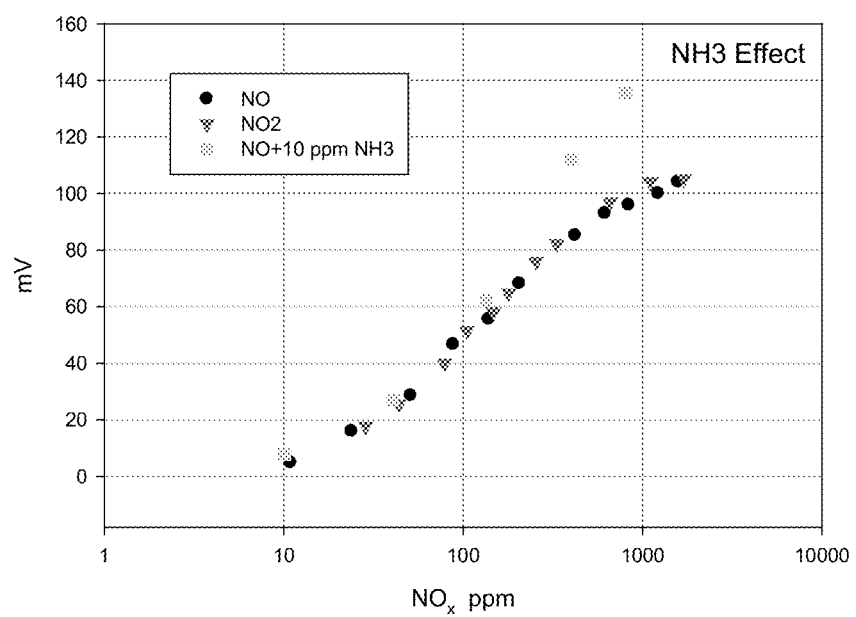
FIG. 14 depicts the effect of combined presence of NOx and NH3 on the PDT response.

FIG. 14 shows that combined presence of NO and NH3 increases sensor outp It is well known that $NH_3$ is undergoing Selective Catalytic Oxidation (SCO) on the surface of Pt:

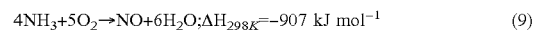

$$4NH_3 + 5O_2 \rightarrow NO + 6H_2O; \Delta H_{298K} = -907 \text{ kJ mol}^{-1} \quad (9)$$

$$4NH_3 + 3O_2 \rightarrow 2N_2 + 6H_2O; \Delta H_{298K} = -1266 \text{ kJ mol}^{-1} \quad (10)$$

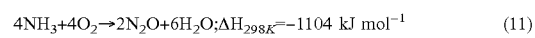

$$4NH_3 + 4O_2 \rightarrow 2N_2O + 6H_2O; \Delta H_{298K} = -1104 \text{ kJ mol}^{-1} \quad (11)$$

Probability of a specific reaction path depends on the specific electrode material and its structure, oxygen surface coverage and reaction temperature. Since PDT was specifically designed to control oxygen surface coverage it can potentially differentiate between competing reactions. First reaction would produce NO and thus result in the output signal from PDT.

It is also possible that $NH_3$ will undergo Selective Catalytic Reduction (SCR) on the surface of Pt as shown in FIG. 1 and equation 12.

$$2NH_3 + NO_2 + NO \rightarrow 2N_2 + 3H_2O \quad (12)$$

This reaction will result in decreased signal from PDT, since it is removing $NO_x$ from the exhaust, leading to reduced interaction with $PtO_x$.

Transient experiments performed over Pt gauze in the Transient Analysis of Product (TAP) reactor have shown that adsorbed oxygen species are crucial for ammonia activation and formation of reaction products. No reaction products were observed when $NH_3$ was pulsed over hydrogen-treated Pt gauze. Apparently a clean platinum surface exhibits a negligible activity for $NH_3$ decomposition for the short residence times ($10^{-3}$ s) achieved in the TAP reactor. However, a Pt gauze catalyst pre-treated in a flow of oxygen at 1073 K revealed a very high activity towards $NH_3$ conversion to $N_2$, $H_2O$ and $H_2$ even in the absence of oxygen from the gas-phase. ut under PDT conditions.

Figure 15:
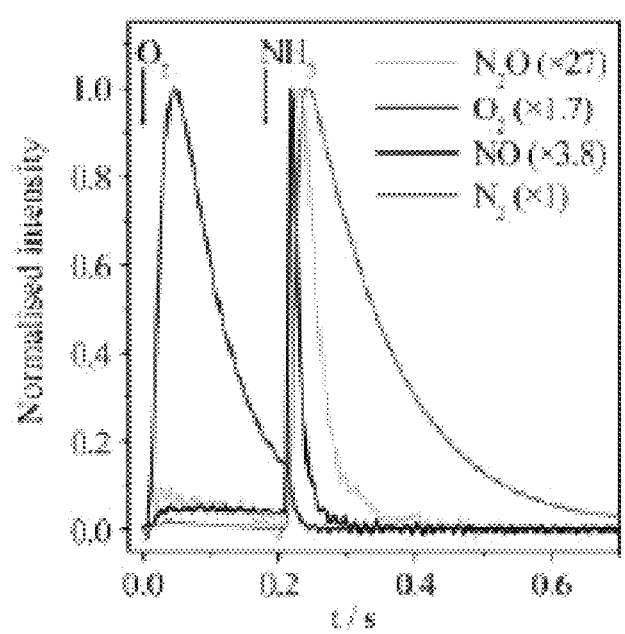
FIG. 15 depicts transient response of the Pt electrode to pulses of O2 and NH3.

Transient experiments performed over Pt gauze in the Transient Analysis of Product (TAP) reactor have shown that adsorbed oxygen species are crucial for ammonia activation and formation of reaction products. No reaction products were observed when NH3 was pulsed over hydrogen-treated Pt gauze. Apparently a clean platinum surface exhibits a negligible activity for NH3 decomposition for the short residence times (10-3 s) achieved in the TAP reactor. However, a Pt gauze catalyst pre-treated in a flow of oxygen at 1073 K revealed a very high activity towards NH3 conversion to N2, H2O and H2 even in the absence of oxygen from the gas-phase. FIG. 15 shows results of the sequential pulsing of O2 and NH3 with a time interval of 0.2 s at 673 K. The steep intensity decrease of the O2 signal, when NH3 enters the reactor indicates a reaction of adsorbed oxygen species with NH3.

Voltage pulses of opposite signs used during the PDT create conditions of oxidation/reduction of Platinum, similar to Oxygen/Hydrogen treatments utilized by Imbihl et al. It is reasonable to expect that interaction between NH3 and oxygen formed during the anodic polarization of the Pt electrode would result in a transient response detectable by the PDT, since pulse durations and temperature range are similar to the test conditions used by Imbihl, Scheibe et al. 2007). Complete reduction of Pt during the cationic cycle will completely inhibit NH3 response. We observed confirmation of a possibility of combined and separate measurements NOx and NH3 under conditions of PDT.

Figure 16A:
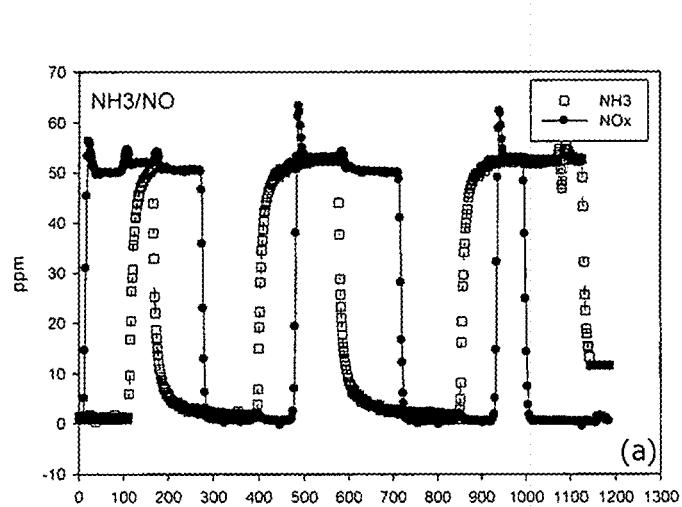
FIG. 16a depicts time dependence of NO and NH3 concentration under the following test conditions: O2=10%; H2O=8%; CO2=8%; Pulse=340 ms; Pause=119 ms, Pulse amplitude=2.5V.
Figure 16B:
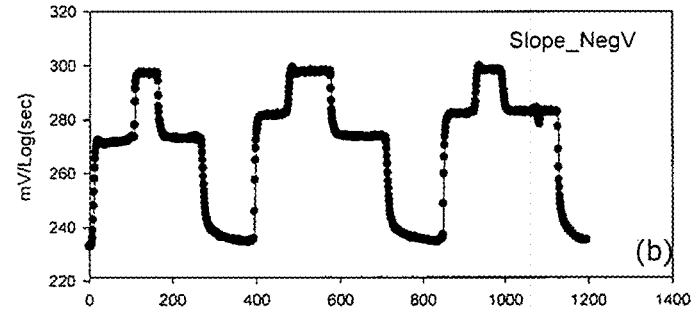
FIG. 16b depicts slope of the discharge curves following negative voltage pulse applied to the inner (reference electrode) of the lambda sensor.

FIG. 16 shows response of the lambda sensor to the pulses of applied NO and NH3 under conditions of PDT. Concentration of applied gas is shown in FIG. 16(a).

Figure 16C:
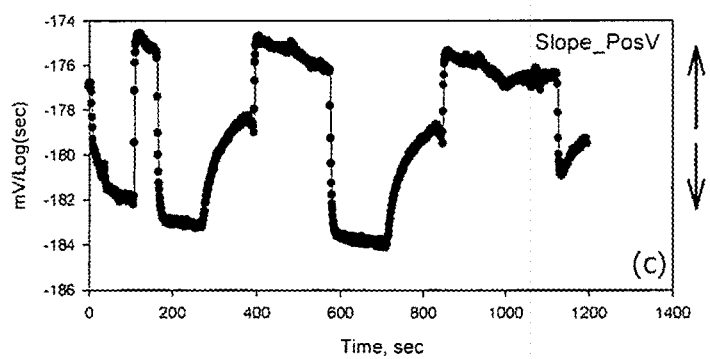
FIG. 16c depicts slope of the discharge curves following positive voltage pulse applied to the inner (reference electrode) of the lambda sensor.
Figures 17A, 17B, 17C:
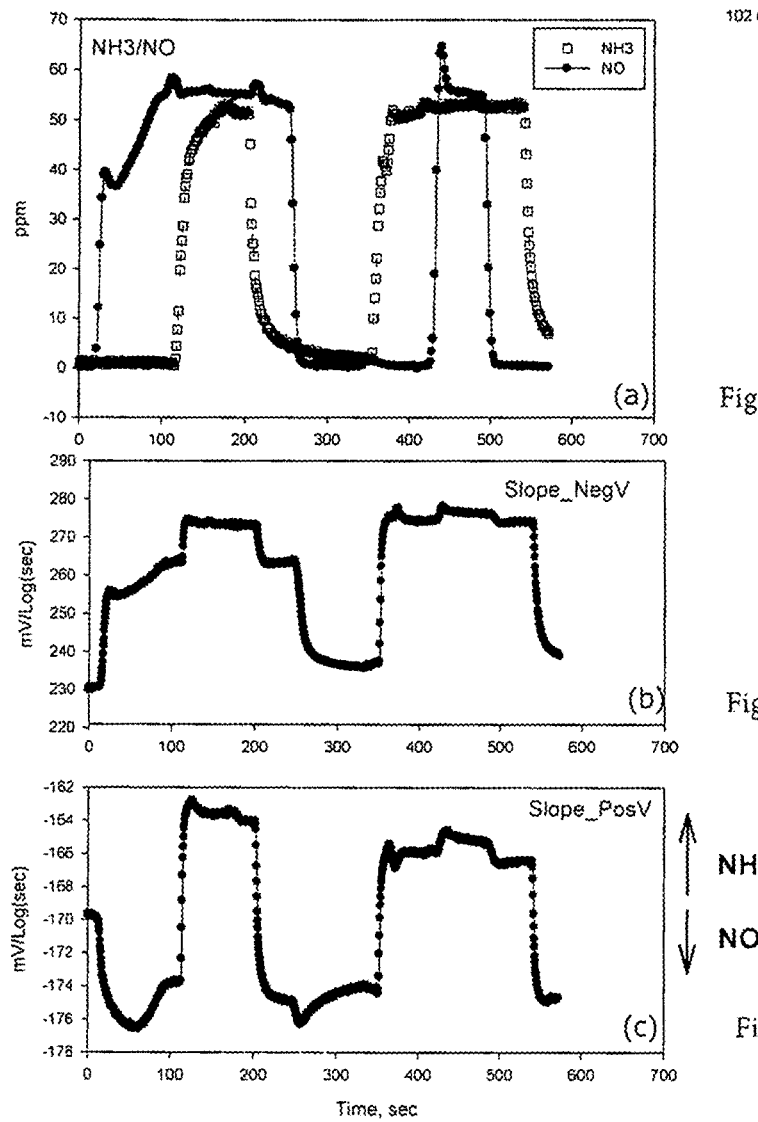
FIG. 17a depicts time dependence of NO and NH3 concentration under the following test conditions: O2=10%; H2O=8%; CO2=8%; Pulse=102 ms; Pause=119 ms, Pulse amplitude=2.5V.
FIG. 17b depicts slope of the discharge curves following negative voltage pulse applied to the inner (reference electrode) of the lambda sensor.
FIG. 17c depicts slope of the discharge curves following positive voltage pulse applied to the inner (reference electrode) of the lambda sensor.
Figures 18A, 18B, 18C:
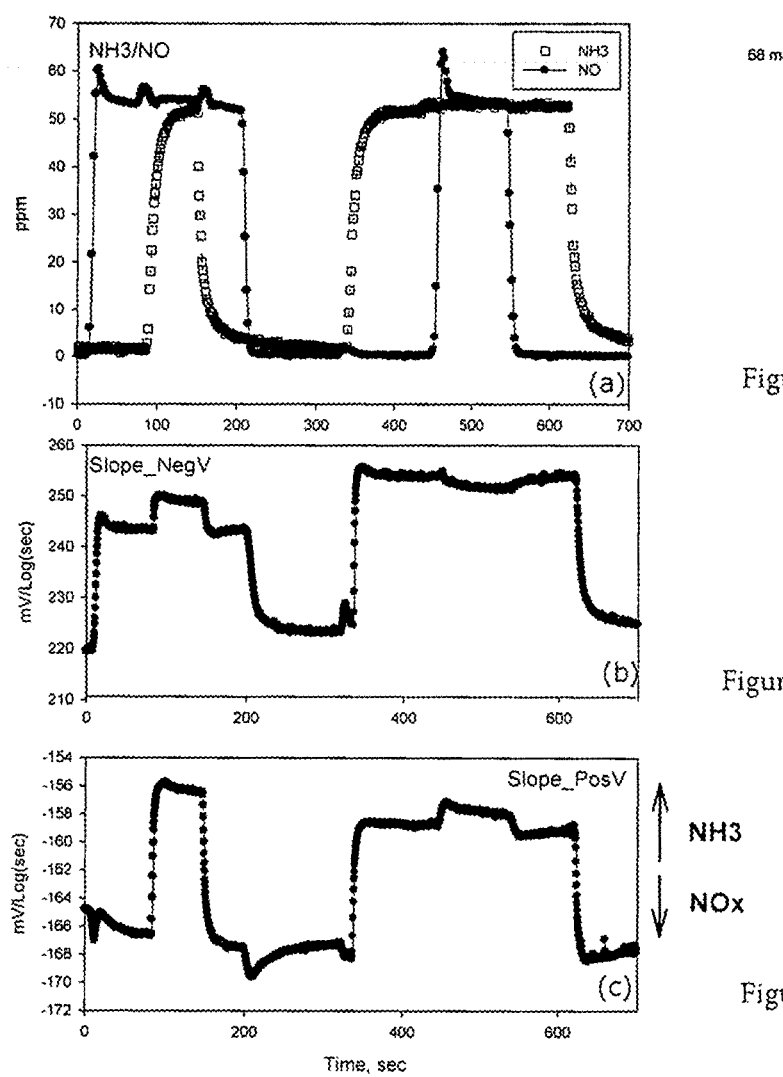
FIG. 18a depicts time dependence of NO and NH3 concentration under the following test conditions: O2=10%; H2O=8%; CO2=8%; Pulse=68 ms; Pause=119 ms, Pulse amplitude=2.5V.
FIG. 18b depicts slope of the discharge curves following negative voltage pulse applied to the inner (reference electrode) of the lambda sensor.
FIG. 18c depicts slope of the discharge curves following positive voltage pulse applied to the inner (reference electrode) of the lambda sensor.

FIG. 16 (b) shows that both NO and NH3 increases absolute value of the slopes of the discharge curves following the negative voltage pulse. Similar to the previously observed results (see FIGS. 13 and 14). However, FIG. 16(c) shows that discharge curves following positive pulses demonstrate different trend. NO increases absolute value of the discharge curves, while NH3 decreases the absolute value of the discharge curves.

FIGS. 16-20 also demonstrate that pulse duration and the order of gas delivery to the measurement Pt electrode has significant effect on the sensor response. In case of sufficiently long pulse duration (~340 ms), increase in the slope of the discharge curves is proportional to the combined concentration of NO+NH3 (See FIG. 16b). For shorter pulse durations (102, 68 and 51 ms), total effect is no longer proportional to the combined concentration of NO+NH3, especially if NH3 is applied first, followed by NO. Increase in the slope of discharge curves reaches saturation (see FIG. 17b-20b). Magnitude of the decrease in the slope of the discharge curves after the positive pulses from its baseline values is increasing proportionally to concentration of NH3, as seen in FIG. 20c.

Figure 21:
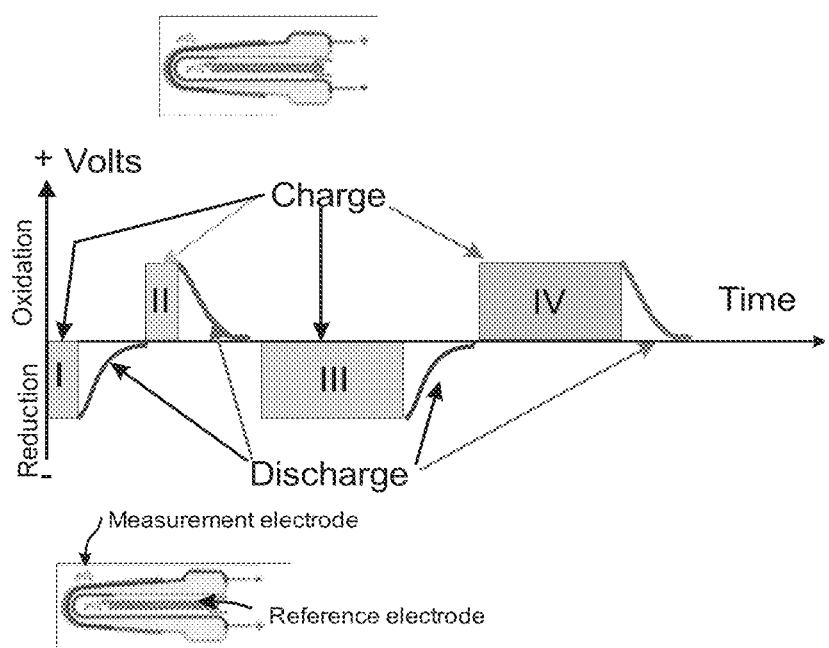
FIG. 21 depicts schematics of the PDT setup for NOx and NH3 measurements

Based on this data we were able to draw a calibration curve as shown in FIG. 21, relating slopes of the discharge curves after the positive pulse with the concentration of NH3. Calculated (measured) values of NH3 by using slopes of the discharge curves after the positive pulse are shown. Measured values of the NH3 concentration are closely tracking applied concentration and most significantly—are not affected by the addition of NO.

Results shown in FIGS. 16-19 clearly demonstrate that both reactions (oxidation and reduction of NH3) are taking place for different signs of the applied voltage pulses. If negative pulse is applied to the inner electrode of the I-sensor, and pulse duration is sufficiently high to deliver oxygen ions to the measurement electrode-oxidation of NH3 is taking place and produce additional amount of NO, thus increasing output of the I-sensor (see FIG. 16b) proportionally to the combined concentration of NO+NH3. If pulse duration is not sufficiently long and is not sufficient to deliver oxygen ions to the measurement electrode, sensor output is no longer proportional to NO+NH3, but react only to one of the gas stream component (NO or NH3) see FIGS. 17-19 b.

In case of the positive pulse applied to the inner electrode of the sensor, measurement electrode is under a strong reduction potential and reduction of NH3 (equation 12) may take place, leading to the decrease in the concentration of NO+NO2 at the measurement electrode and to the decrease in the discharge slopes (see FIGS. 16-19c).

3. Expected Mechanism of Ammonia Detection by Using Pulse Discharge Technique

Figure 20A:
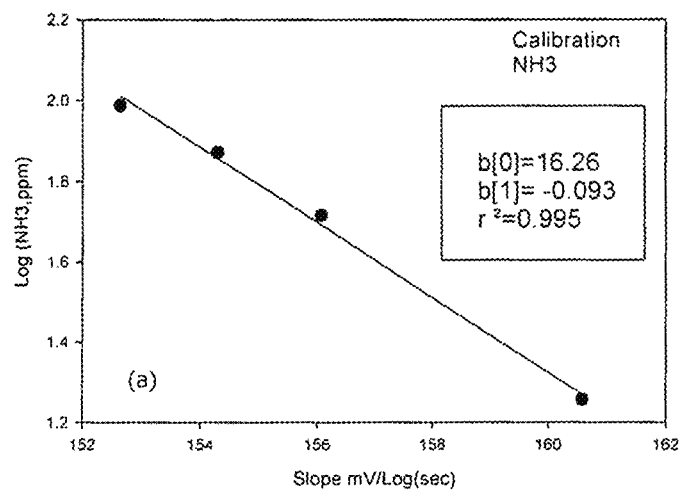
FIG. 20a depicts calibration curve relating concentration of applied ammonia with the slope of discharge curve after the positive pulse.
Figure 20B:
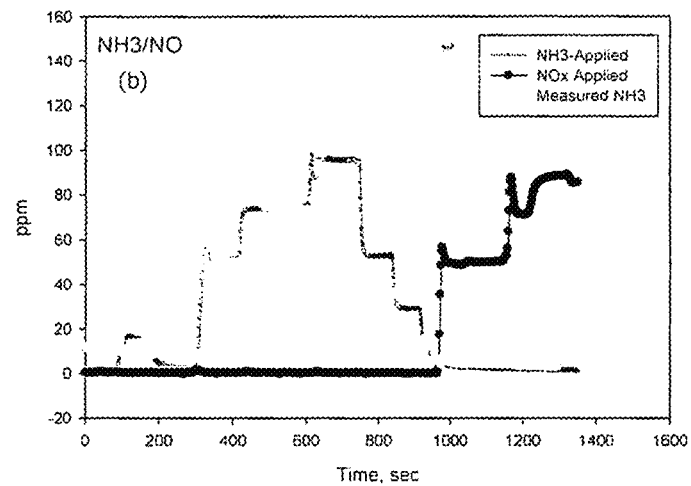
FIG. 20b depicts measured NH3 concentration.

Voltage Pulses used in the PDT create conditions for oxidation reduction of Platinum electrode. Variation of the pulse duration will provide controllable amount of oxygen ions available for oxidation of ammonia per reactions 9-11. Variation of the sensor temperature will also control reaction path between oxidation or reduction of ammonia (equations 9-11 versus equation 12). Reactions 9 and 11 will increase apparent concentration of NO; reaction 12 will decrease NO concentration; reaction 10, should not have any effect on NO concentration. In our preliminary tests we observed that both effects are possible. FIGS. 16-19 shows that both effects of increase and decrease of the slopes of the discharge curves can be observed. Combined concentration of the NOx+NH3 can be measured by the increase in the slopes of the discharge curves after the negative pulse, while individual concentration of NH3 can be measured from the slopes of the discharge curves after positive pulse and using the calibration curve similar the one shown in FIG. 20a. FIG. 20b shows measured NH3 concentration, which closely follow applied values of the NH3 concentration. Thus measured NH3 concentration is not affected by subsequently applied NO. Individual concentrations of NOx and NH3 can be then measured as a difference in the total concentration of NOx+NH3 and NH3.

Separate effect of NH3 versus NOx can be also achieved by varying pulse duration and limiting amount of oxygen available for oxidation reactions of NH3. Changes in the NH3 versus NOx signals are detected by shape and slope of the discharge curves during the pauses separating the pulses. It is assumed that at short pulse durations, only NOx reaction with PtOx will be prevalent (equations 6-7). At longer pulse durations we can control reaction path between oxidation or reduction of NH3. By comparing discharge slopes for short (~51 ms) and long (~340 ms) pulses we will be able to separate effect of NOx and NH3.

Schematics of the proposed method is shown in FIG. 21. Measurement cycle will consist of the four pulse/pause cycles. First two positive/negative pulses are set for a short pulse duration (~51 ms), second set positive/negative pulses are set for a longer pulse duration (~340 ms). Pause durations will remain the same for all 4 cycles (~120 ms). By comparing discharge curves after short and long negative pulses we will be able to extract information about concentration of NH3 and NO present in the exhaust. To enhance differences in the NOx versus NH3 reaction rate with PtO, we will also vary temperature and catalytic activity of Pt electrode by addition of Rh in the concentration range 5-20%. It was shown by Kondratenko, Kraehnert et al. 2006 that catalytic activity of Pt electrodes for NH3 oxidation (see equation 9-11), depends on the concentration of Rh in the Pt/Rh electrodes. Observed results were related to formation of Rh2O3 and PtOx. PDT is uniquely suitable for controlling conditions for oxidation/reduction of PtOx and Rh2O3.

The foregoing descriptions of specific embodiments of the present invention are presented for purposes of illustration and description. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of *Warner-Jenkinson Company*, v. *Hilton Davis Chemical*, 520 US 17 (1997) or *Festo Corp.* v. *Shoketsu Kinzoku Kogyo Kabushiki Co.*, 535 U.S. 722 (2002), or other similar case-law or subsequent precedent should not be made if any future claims are added or amended subsequent to this Patent Application.

What is claimed is:

1. A method for measuring either NOx and NH3 in a gas stream with a single sensor having sensor electrodes, the method comprising the steps:
   a. exposing a sensor electrode of said sensor to a gas stream containing a mixture of different gases including NOx and NH3;
   b. subjecting said sensor electrode to the conditions of the Pulse Discharge Technique (PDT) with fixed durations of the positive pulses, negative pulses and pauses between the pulses;
   c. measuring combined concentration of NOx and NH3 by:
      i. measuring rates of change of the slope of the discharge curve $V_{d,neg}(t) = \text{constant} + \text{slope} * \log(t)$ where (t) is the time elapsed time during a pause after a negative pulse, and $V_{d,\ neg}(t)$ is the discharge volume measured between the sensor electrodes following a negative pulse applied between the sensor electrodes;
      ii. determining the slopes for a series of discharge curves after negative pulses; and
      iii. relating a rate of change in these slopes to the combined concentration of NOx and $NH_3$;
   d. measuring separate concentration of NH3 alone by
      i. measuring the slope of the discharge curve $V_{d,pos}(t) = \text{constant} + \text{slope} * \log(t)$, wherein t is the time elapsed during a pause after a positive pulse, and $V_{d,\ pos}(t)$ is the discharge voltage measured between the sensor electrodes following a positive pulse applied between the sensor electrodes;
      ii. determining the slopes for a series of discharge curves after positive pulses; and
      iii. relating a rate change in these slopes to the concentration $NH_3$;
   e. determining the concentration of NOx alone by subtracting the measured concentration of $NH_3$ from the combined concentration of NOX and $NH_3$.

2. The method of claim 1, further comprising:
   i. manipulating said combined concentration of NOx and $NH_3$ through varying oxidation/reduction of the $NH_3$ on the sensor electrode by varying sensor electrode temperature in the range of 280 to 450° C.;
   j. manipulating said combined concentration of NOx and $NH_3$ through varying for oxidation/reduction of the $NH_3$ on the sensor electrode by varying duration of the PDT pulses in the range from 3 to 500 ms and the durations of the PDT pauses in the range 100-500 ms; and
   k. manipulating said combined concentrations of NOx and $NH_3$ conditions for oxidation/reduction of the NH3 on the sensor electrode by varying amplitude of the pulses of the PDT in the range from 0.5 to 3V.

3. The method of claim 1, further comprising:
   a. manipulating said combined concentration of NOx and $NH_3$ through varying oxidation/reduction of the $NH_3$ and its reaction with NOx on the sensor electrodes by varying duration of the pulses and pauses during PDT;
   b. applying a short positive pulse between the sensor electrode with the duration between 3 and 100 ms;
   c. pausing said short positive pulse with the duration 100-500 ms;
   d. applying a short negative pulse between the sensor electrode with the duration between 3 to 100 ms;
   e. said short negative pulse is followed by the pause with the same duration as the preceding pause after short positive pulse;
   f. applying a long positive pulse with a duration of 100-500 ms;
   g. said long positive pulse is followed by the pause with the duration 100-500 ms
   h. applying a long negative pulse with the same duration as the preceding long positive pulse;
   i. said long negative pulse is followed by the pause with the same duration as preceding pause after the long positive pulse;
   measuring slopes of the discharge curves during the pauses following short and long positive and negative pulses;
   k. comparing slopes of the discharge curves following positive and negative pulses; and
   l. extracting information concerning concentration of NH3 and NO from the differences in the slopes of the discharge curves following short and long pulses.

* * * * *